United States Patent [19]
Brands et al.

[11] Patent Number: 6,060,607
[45] Date of Patent: May 9, 2000

[54] PROCESS FOR SYNTHESIZING CARBAPENEM SIDE CHAIN INTERMEDIATES

[75] Inventors: Karel M. J. Brands, Jersey City; John M. Williams, Belle Mead; Ulf H. Dolling, Westfield; Ronald B. Jobson, East Brunswick, all of N.J.; Antony J. Davies, Hertford Heath, United Kingdom; Ian F. Cottrell, Hertford, United Kingdom; Mark Cameron; Michael S. Ashwood, both of Bishops Stortford, United Kingdom

[73] Assignee: Merck & Co., Inc., Rahway, N.J.

[21] Appl. No.: 09/334,398

[22] Filed: Jun. 16, 1999

Related U.S. Application Data

[62] Division of application No. 09/106,297, Jun. 29, 1998.
[51] Int. Cl.[7] .................. C07D 207/10; C07F 9/572
[52] U.S. Cl. ............................ 548/412; 548/537
[58] Field of Search ........................ 548/412, 537

[56] References Cited

U.S. PATENT DOCUMENTS

| | | |
|---|---|---|
| 4,340,738 | 7/1982 | Sipido . |
| 5,648,501 | 7/1997 | Brands et al. ................ 548/453 |

FOREIGN PATENT DOCUMENTS

| | | |
|---|---|---|
| 0 551 993 A1 | 7/1993 | European Pat. Off. . |
| WO 97/06154 | 2/1997 | WIPO . |

OTHER PUBLICATIONS

Brands et al., Tetrahedron Letters, vol. 37, No. 17, pp. 2919–2922, Apr. 22, 1996.

*Primary Examiner*—Laura L. Stockton
*Attorney, Agent, or Firm*—Sylvia A. Ayler; Mark R. Daniel

[57] ABSTRACT

A process of synthesizing a compound of the formula 1:

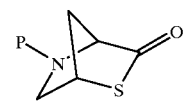

1 is described. A compound of the formula 2:

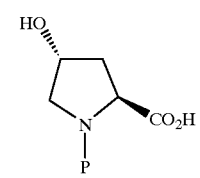

2 is reacted with diphenylphosphinic chloride to activate the carboxylic acid group, and then reacted with methanesulfonyl chloride to produce a compound of formula 4:

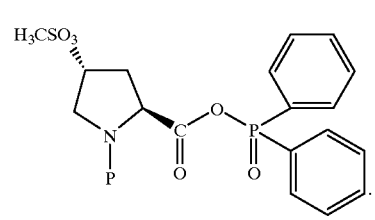

4

Compound 4 is then reacted with a group II metal sulfide source in water to produce a compound of formula 1.

18 Claims, No Drawings

PROCESS FOR SYNTHESIZING CARBAPENEM SIDE CHAIN INTERMEDIATES

This is a division of application Ser. No. 09/106,297, filed Jun. 29, 1998.

BACKGROUND OF THE INVENTION

The present invention relates to the synthesis of carbapenem side chains, and in particular, to side chains or portions thereof containing a pyrrolidine group, which is bonded to the carbapenem nucleus through a thioether linkage. Typically, the pyrrolidine is a portion of the side chain, and is substituted at the two position with any of a variety of substituents.

Conventionally, these intermediate compounds are prepared from a 4-hydroxyproline derivative of the formula:

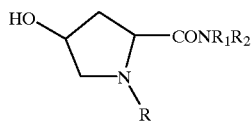

Such synthetic schemes typically require the extensive use of protecting groups.

Similarly, a method of converting trans-4-hydroxy-L-proline to a thiolactone of the formula:

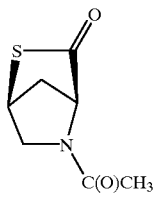

has been described. However, this thiolactone is unsuitably protected for synthesis of carbapenem antibiotics.

EP 551 993 A1 published on Jul. 21, 1993 relates to a synthesis which utilizes active esterifying agents and base, followed by treatment with hydrogen sulfide, or an alkali metal salt of hydrogen sulfide, and base.

The present invention is an improvement over these other processes, utilizing a sulfide source which surprisingly improves the process when commercial quantities are synthesized.

SUMMARY OF THE INVENTION

A process for synthesizing a compound of the formula 1:

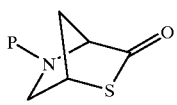

is described wherein P is a protecting group comprising (a) reacting a compound of formula 2:

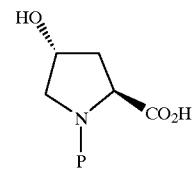

wherein P is as previously defined with diphenylphosphinic chloride to produce a compound of formula 3:

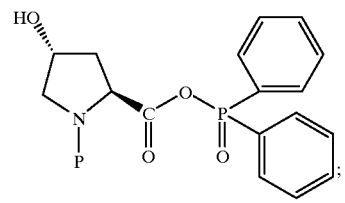

(b) reacting compound 3 with methanesulfonyl chloride to produce a compound of formula 4:

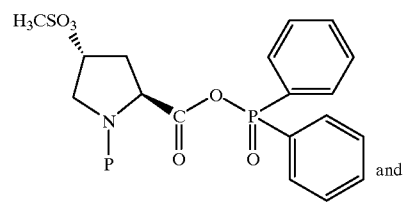

and (c) combining compound 4 with an alkali metal sulfide or non-alkali metal sulfide in water to produce a compound of formula 1.

More particularly, the process described herein relates to a process for producing a compound of the formula 5:

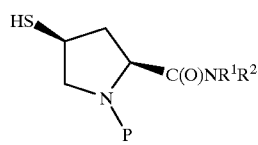

wherein P is a protecting group;

$R^1$ and $R^2$ are independently selected from hydrogen, aryl and heteroaryl, said aryl and heteroaryl groups being unsubstituted or substituted with from 1–3 groups selected from the group consisting of: $C_{1-4}$ alkyl, $C_{1-4}$ alkoxy, $C_{1-4}$ alkylthio, halo, hydroxy, $CO_2H$, $CO_2C_{1-4}$ alkyl, $NH_2$, $NHC_{1-4}$ alkyl, $N(C_{1-4}$ alkyl$)_2$, $SO_3H$, CN, $NHC(O)C_{1-4}$ alkyl, $SO_2NH_2$, $SO_2C_{1-4}$ alkyl, aryl and heteroaryl;

comprising: (a) reacting a compound of the formula 2:

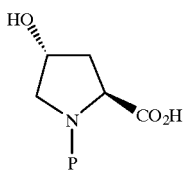

wherein P is as previously defined with diphenylphosphinic chloride to produce a compound of the formula 3:

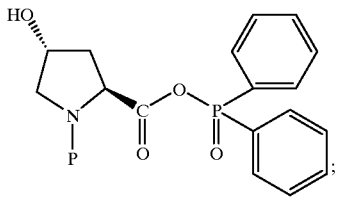

(b) reacting compound 3 with methanesulfonyl chloride to produce a compound of formula 4:

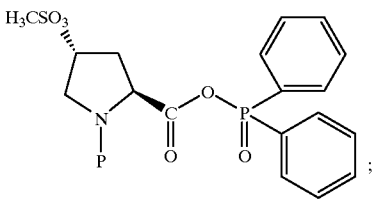

(c) combining compound 4 with an alkali metal sulfide or non-alkali metal sulfide in water to produce a compound of formula 1:

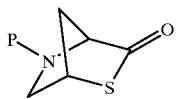

and (d) reacting compound 1 with $NHR^1R^2$ wherein $R^1$ and $R^2$ are as previously defined to produce a compound of formula 5.

DETAILED DESCRIPTION OF THE INVENTION

The invention is described using the following definitions unless otherwise specified.

Alkyl and the alkyl portions of substituent groups include monovalent hydrocarbon chains containing from 1–4 carbon atoms which are straight or branched as appropriate.

Aryl refers to 6–10 membered mono- and bicyclic ring systems, containing carbon atoms with alternating (resonating) double bonds. Preferred aryl groups are phenyl and naphthyl.

Heteroaryl refers to aromatic 5–10 membered mono- and bicyclic ring systems, containing from 1–4 heteroatoms, O, S or N. Preferred nitrogen containing monocyclic heteroaryl groups include pyridyl, pyrimidinyl, pyrazinyl, pyrrolyl, imidazolyl, thiazolyl, oxazolyl and 1,2,4-triazolyl. Preferred heteroaryl groups containing oxygen as the only heterotom include furanyl. Preferred heteroaryl groups containing sulfur as the only heterotom include thienyl.

Preferred bicyclic heteroaryl groups include benzthiazolyl, benzimidazolyl, quinolinyl and isoquinolinyl, indolyl and isoindolyl.

When substituted, the aryl and heteroaryl groups may be substituted with 1–3 groups selected from the group consisting of: $C_{1-4}$ alkyl, $C_{1-4}$ alkoxy, $C_{1-4}$ alkylthio, halo, hydroxy, $CO_2H$, $CO_2C_{1-4}$ alkyl, $NH_2$, $NHC_{1-4}$ alkyl, $N(C_{1-4}$ alkyl$)_2$, $NHC(O)C_{1-4}$ alkyl, $SO_3H$, $CN$, $SO_2NH_2$, $SO_2C_{1-4}$ alkyl, aryl and heteroaryl.

When necessary, the substituents which are optionally present on aryl and heteroaryl can be in protected form.

Examples of suitable protecting groups include the following without limitation: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl (t-BOC), 2,2,2-trichloroethyloxycarbonyl benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl) ethyl, phenacyl, p-methoxybenzyl, acetonyl, p-methoxyphenyl, 4-pyridylmethyl, t-butyl, allyloxycarbonyl, di—$C_{1-10}$ alkylphosphoryl, diarylphosphoryl and di—ar—$C_{1-10}$ alkylphosphoryl. Preferred silyl protecting groups are trimethylsilyl and triethylsilyl. Preferred carboxyl protecting groups are p-nitrobenzyl and allyl. Preferred phosphoryl based protecting groups include diisopropylphosphoryl.

Many other suitable hydroxyl and carboxyl protecting groups are known in the art. See, e.g., Greene, T. W., et al. *Protective Groups in Organic Synthesis*, John Wiley & Sons, Inc., 1991.

P represents a protecting group on the proline nitrogen atom. Thus, in one aspect of the invention, P represents a member selected from the group consisting of: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl (t-BOC), 2,2,2-trichloroethyloxycarbonyl benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl) ethyl, phenacyl, p-methoxybenzyl, acetonyl, p-methoxyphenyl, 4-pyridylmethyl, t-butyl, allyloxycarbonyl, di—$C_{1-10}$ alkylphosphoryl, diarylphosphoryl and di—ar—$C_{1-10}$ alkylphosphoryl.

More particularly, P represents a protecting group which is selected from the group consisting of: t-BOC, diisopropylphosphoryl and p-nitrobenzyloxycarbonyl.

Most particularly, P represents diisopropylphosphoryl.

Compound 2 used herein as a starting material is N protected trans-4-hydroxy-L-proline. The 2-carboxyl group is activated using the compound diphenylphosphinic chloride, which is reacted with compound II in a solvent in the presence of excess base. Solvents which are useful herein include dichloromethane, acetonitrile, toluene, fluorobenzene, tetrahydrofuran, or mixtures thereof. Bases which are useful for this reaction include trialkylamines. Preferred trialkylamines include diisopropylethylamine (DIPEA) and triethylamine.

Typically an amount of diphenylphosphinic chloride which is about equimolar to the starting compound can be used. The reaction between compound 2 and diphenylphosphinic chloride is typically run at reduced temperature, below about 0° C. to as low as about −40° C. Preferably, the reaction temperature is maintained at about −10° C.

Compound 3, with the diphenylphosphinyloxycarbonyl group at position two, is reacted with methanesulfonyl chloride (MsCl) to produce compound 4. This reaction is conducted in a solvent, in the presence of a slight molar excess of pyridine, collidine, lutidine and the like, using a slight molar excess of MsCl. This mesylation reaction may be conducted over about 1–4 hours, at a reduced temperature, e.g., about 0° C. to as low as about −40° C. Preferably, the reaction temperature is maintained at about −10° C.

Compound 4 is thereafter combined with an alkali metal sulfide or non-alkali metal sulfide and water to form the thiolactone 1. Essentially the reaction can be conducted at about −10° C. to about room temperature. Preferably the sulfide and water are added quickly, and the reaction is aged for several hours at ambient temperature.

As used herein, "alkali metal sulfide" refers to the group I metal sulfides, such as the sulfides of sodium and potassium. Preferably the alkali metal sulfide is $Na_2S$.

As used herein, "non-alkali metal sulfides" and "alkaline earth metals" are used interchangeably to include the group II alkaline earth metal sulfides selected from the group consisting of: magnesium, calcium and barium. Preferred are calcium and barium.

The preferred non-alkali metal sulfide, most notably CaS, provides an unexpected advantage in that side products of the reaction have low solubility in water, and thus can be removed as a precipitate.

In a preferred aspect of the process described herein, the amine $HNR^1R^2$ is m-aminobenzoic acid.

In another preferred aspect of the process, the compound of formula 5 is reacted with an acid to produce a compound of formula 6:

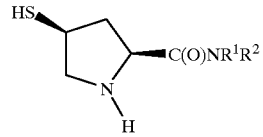

More particularly, a compound of formula 2':

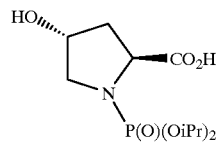

is reacted with diphenylphosphinic chloride to produce a compound of formula 3':

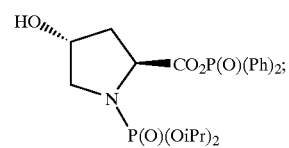

compound 3' is reacted with mesyl chloride to produce compound 4':

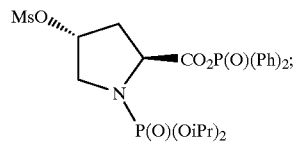

compound 4' is reacted with a member selected from the group consisting of: $Na_2S$, $K_2S$, CaS and BaS to produce a compound of formula 1':

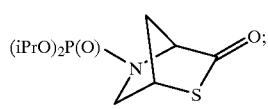

compound 1' is reacted with m-aminobenzoic acid to produce 5':

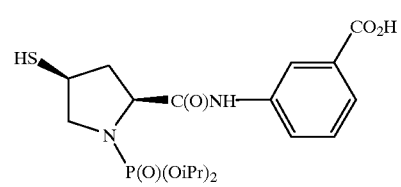

and compound 5' is reacted with acid to produce a compound of formula 6':

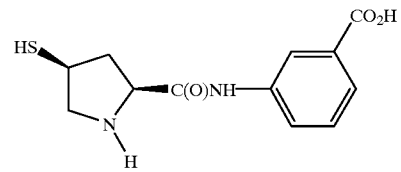

or a salt or solvate thereof.

In a preferred aspect of the invention, the thiolactone compound 1 is reacted with the amine $HNR^1R^2$ in the presence of an organic acid to produce compound 5. Examples of suitable organic acids include formic acid, acetic acid and propionic acid. Most preferably, the reaction is conducted in the presence of acetic acid.

After the conversion of compound 4' to compound 1', the latter is combined with ammonia or a primary or secondary amine to form compounds of formula 5', which can be deprotected to give compound 6' or salt thereof. In the isolation of 6' solvents, such as $C_{1-5}$ alcohols, $C_{1-3}$ alkanoic acids, toluene, acetonitrile, ethyl acetate and others may be added to improve crystallization, or otherwise facilitate isolation. Also, addition of a trialkyl or triaryl phosphine, e.g., tri-n-butylphosphine, at this stage may be useful in reducing the formation of disulfides corresponding to compound 6' and/or improving the rejection of other impurities.

Most primary and secondary amines $HNR^1R^2$ wherein $R^1$ and/or $R^2$ represent H, aryl or heteroaryl react with compound 1 upon slight heating. Generally, the reaction proceeds from about RT to about 100° C. over a few minutes to several hours.

The acid that is used to convert compound 5' to compound 6' can be varied within wide limits. For example, concentrated HCl can be used and is preferred.

The invention described herein can be conducted in essentially a single reaction vessel, thus allowing for economical production of compounds 6' from compound 2.

The invention is further illustrated with the following non-limiting examples.

EXAMPLE ONE (1S, 4S)-5-DIISOPROPYLPHOSPHORYL-2-THIA-5-AZABICYCLO[2.2.1]HEPTAN-3-ONE

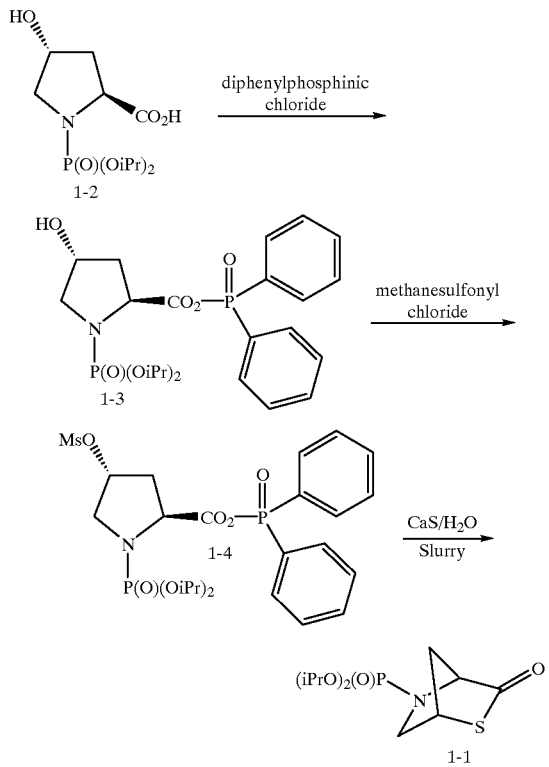

The following starting materials were utilized:

| Starting Material | Quantity |
| --- | --- |
| Diisopropylphosphoryl hydroxyproline | 5.0 g, 16.93 mmol |
| Diisopropylethylamine | 6.34 mL, 36.44 mmol |
| Diphenylphosphinic chloride | 3.36 mL, 17.61 mmol |
| Pyridine | 1.48 mL, 18.29 mmol |
| Methanesulfonyl chloride | 1.43 mL, 18.46 mmol |

-continued

| Starting Material | Quantity |
| --- | --- |
| Calcium sulfide | 1.49 g, 20.66 mmol |
| Dichloromethane | 100 mL |
| Water | 350 mL |

The mesylate mixed anhydride was formed according to WO 97/06154 published on Feb. 20, 1997, incorporated herein by reference, and stirred with cooling at −15° C. for 15 min.

Calcium sulfide (1.49 g) was added as a solid and washed with water (30 mL), resulting in a three phase reaction mixture. The mixture was stirred rapidly and the cooling bath removed, allowing the mixture to reach room temperature.

The solids quickly went into solution, and a white solid precipitate was formed.

The mixture was stirred for 45 min and then filtered through a coarse filter. The solid on the filter was washed with dichloromethane and the filtrate separated.

The organic layer (approx. 200 mL) was washed with 1 M HCl (50 mL), and 8% $NaHCO_3$ (50 mL). The aqueous bicarbonate layer was back extracted and the combined extracts were washed with brine and the layers weighed. The presence of the title compound (4.04 g) was confirmed by HPLC.

EXAMPLE TWO

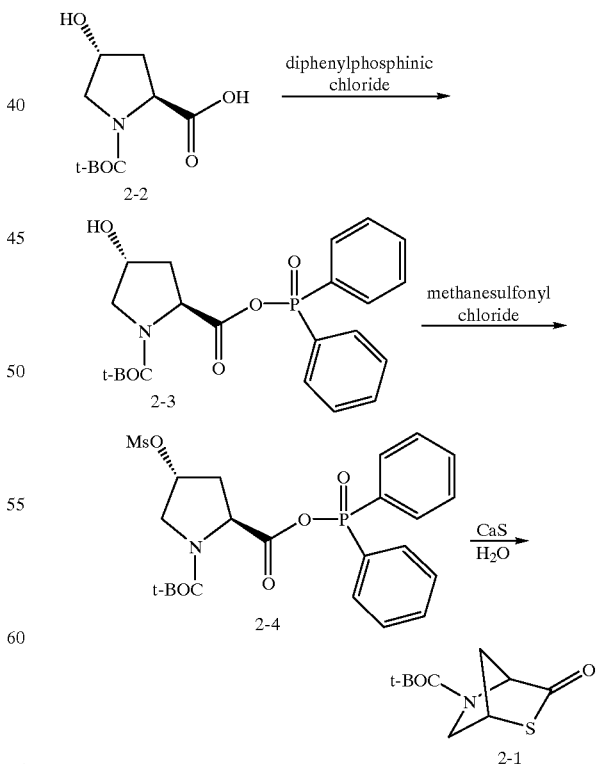

A. Synthesis of trans-N—t-butoxycarbonyl-2-diphenylphosphinyloxycarbonyl-4-hydroxy-L-proline

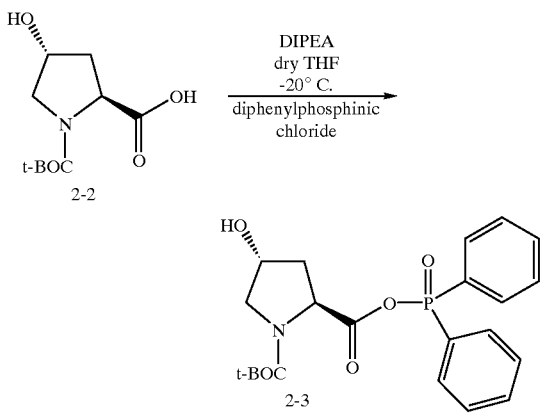

A solution of compound 2—2 (35.0 g, 151 mmol.) and DIPEA (60 mL, 344 mmol) in dry THF (1.0 L) was combined over 20 min with a solution of diphenylphosphinic chloride (37.5 g, 155 mmol) in THF (50 mL) at −20° C. The reaction mixture was stirred at −20° C. for 90 minutes to produce compound 2–3, which can be isolated and characterized or used in the next part without isolation.

B. Synthesis of trans-N—t-butoxycarbonyl-2-diphenylphosphinyl oxycarbonyl-4-methanesulfonyloxy-L-proline

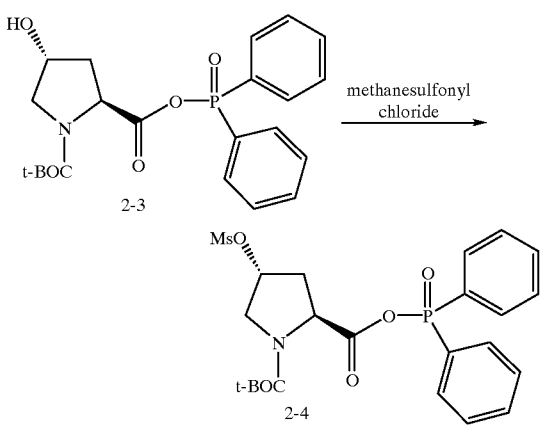

Without isolation and characterization, after stirring the reaction mixture from part A for 90 minutes at −20° C., pyridine (13.0 mL, 161 mmol) was added followed by a solution of methanesulfonyl chloride (19.8 g, 171 mmol) in THF (50 mL) over 15 minutes. The reaction mixture was stirred at −20° C. for 2 hours and allowed to warm to −5° C. over an additional 30 minutes producing compound 2–4. The methanesulfonyl substituted compound can be isolated and characterized, or used in the next reaction without isolation and characterization.

C. Synthesis of N—t-butoxycarbonyl-2-thia-5-azabicyclo[2.2.1]heptan-3-one

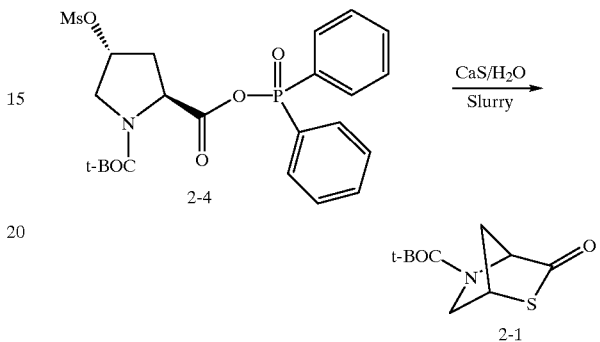

After allowing the reaction from part B to warm to −5° C., a slurry of CaS (45.0 g, 187 mmol) in $H_2O$ (60 mL) is added in one portion. The mixture is allowed to warm to room temperature and is stirred for 6 hrs. The resulting suspension is filtered and the filtrate is then partitioned between toluene and water. The organic layer is washed with HCl (2.0 M), $NaHCO_3$ (1.0 M) and brine, dried over $MgSO_4$ and concentrated in vacuo.

EXAMPLE THREE

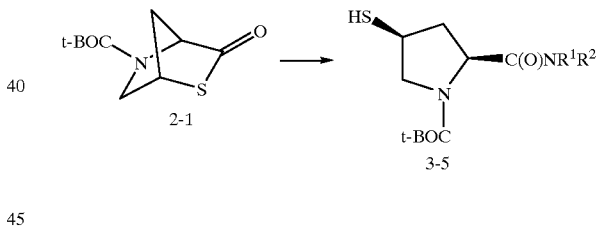

The thiolactone 2-1 from Example Two without isolation, can be combined with the amine shown below in column one to produce the cis N-protected 4-thiol substituted proline derivative shown below in column two.

TABLE ONE

| Amine | Product (3) |
|---|---|
| (3-1)<br>$NH_4Cl$ | HS⟨pyrrolidine⟩C(O)$NH_2$<br>t-BOC<br>3-5-1 |

TABLE ONE-continued

| Amine | Product (3) |
|---|---|
| (3-2) aniline | 3-5-2 |
| (3-3) 3-aminobenzoic acid | 3-5-3 |
| (3-4) 5-amino-2-carboxythiophene | 3-5-4 |
| (3-5) 3-aminobenzoic acid | 3-5-5 |

(1) 4.0 eq. of $NH_4Cl$ in $Et_3N$; solvent $CH_3OH$; reaction time: 30 min at RT;
(2) 1.25 eq. of aniline; solvent toluene; reaction time: 2 hrs at 100° C.;
(3) 1.25 eq. of 3-aminobenzoic acid; solvent toluene; reaction time: 2 hrs at 100° C.;
(4) 1.25 eq. of 5-amino-2-carboxythiophene; solvent toluene; 2 hrs at 100° C.;
(5) P represents diisopropylphosphoryl. (iPr = isopropyl).

EXAMPLE FOUR

Using the procedures set forth in Example Two, Part A, the compounds of column one are reacted with diphenylphosphinic chloride to produce the compounds in column two.

TABLE TWO 4-2-1

4-3-1

Ph = phenyl

TABLE TWO-continued

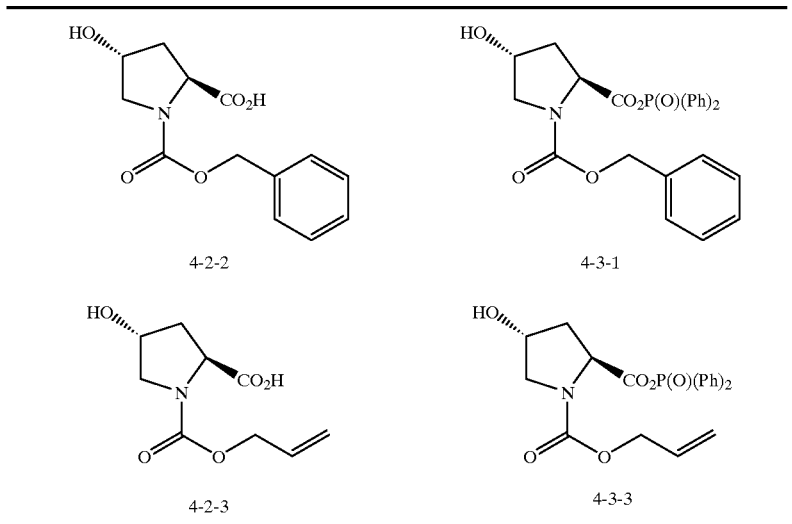

EXAMPLE FIVE

Using the procedures set forth in Example One, Part B, the compounds of column one are reacted with methanesulfonyl chloride to produce the compounds in column two.

TABLE THREE

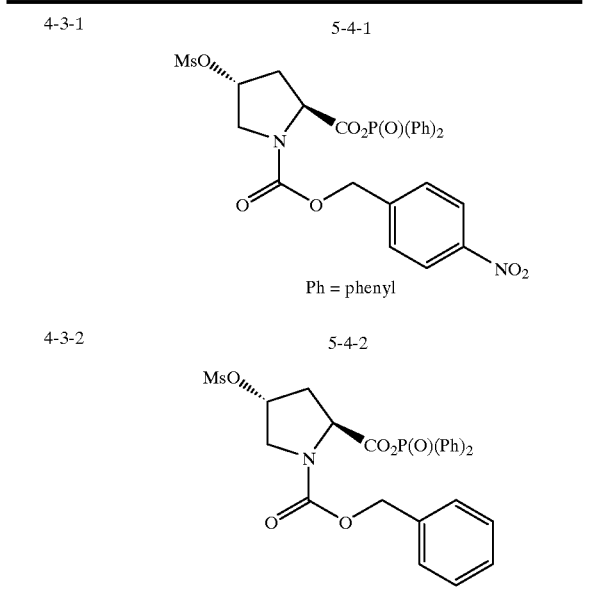

EXAMPLE SIX

Using the procedures set forth in Example Two, Part C, the compounds of column one are reacted with CaS in water to produce the compounds in column two.

TABLE FOUR

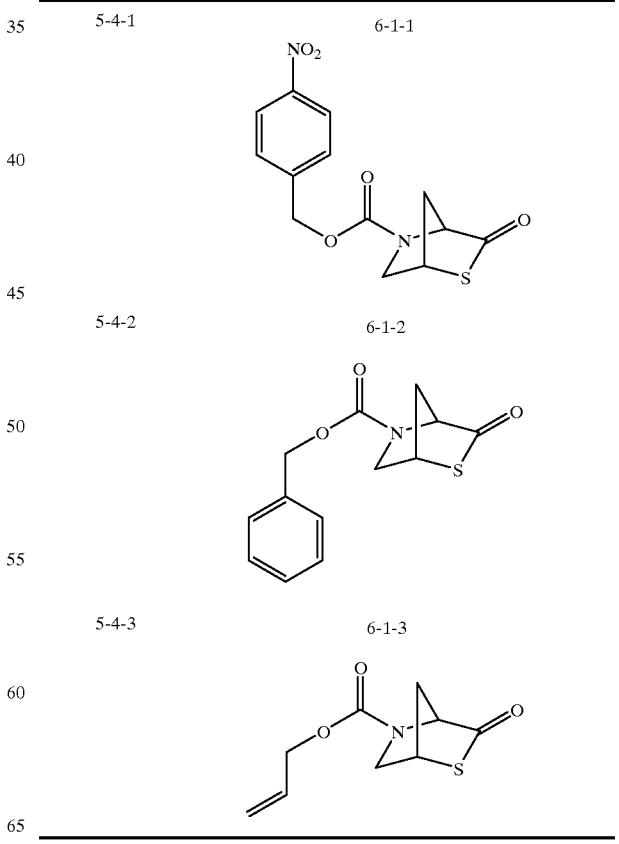

EXAMPLE SEVEN

Using the procedures set forth in Example Three, the compounds of column one are reacted with the amine in column two to produce the compounds in column three.

TABLE FIVE

| | Amine NHR$^1$R$^2$ | Pyrrolidine |
|---|---|---|
| 6-1-1 | (1) NH$_4$Cl | 7-5-1$^1$ |
| 6-1-1 | (2) aniline (NH$_2$-phenyl) | 7-5-2$^1$ (Ph = Phenyl) |
| 6-1-1 | (3) 3-aminobenzoic acid | 7-5-3$^1$ |
| 6-1-1 | (4) 5-amino-thiophene-2-carboxylic acid | 7-5-4$^1$ |
| 6-1-2 | (1) NH$_4$Cl | 7-5-5$^1$ |

TABLE FIVE-continued

| Amine NHR$^1$R$^2$ | | Pyrrolidine |
|---|---|---|
| 6-1-2 | (2) aniline (NH$_2$-Ph) | 7-5-6[1] (2S,4S)-4-mercapto-1-(benzyloxycarbonyl)-N-phenyl-pyrrolidine-2-carboxamide; Ph = Phenyl |
| 6-1-2 | (3) 3-aminobenzoic acid | 7-5-7[1] (2S,4S)-4-mercapto-1-(benzyloxycarbonyl)-N-(3-carboxyphenyl)-pyrrolidine-2-carboxamide |
| 6-1-2 | (4) 5-amino-thiophene-2-carboxylic acid | 7-5-8[1] (2S,4S)-4-mercapto-1-(benzyloxycarbonyl)-N-(5-carboxythiophen-2-yl)-pyrrolidine-2-carboxamide |
| 6-1-3 | (1) NH$_4$Cl | 7-5-9[1] (2S,4S)-4-mercapto-1-(allyloxycarbonyl)-pyrrolidine-2-carboxamide |
| 6-1-3 | (2) aniline | 7-5-10[1] (2S,4S)-4-mercapto-1-(allyloxycarbonyl)-N-phenyl-pyrrolidine-2-carboxamide; Ph = Phenyl |

TABLE FIVE-continued

| | Amine NHR¹R² | | Pyrrolidine |
|---|---|---|---|
| 6-1-3 | (3) | 7-5-11[1] | |
| | 3-aminobenzoic acid | | HS-pyrrolidine-N(alloc)-C(O)NH-3-carboxyphenyl |
| 6-1-3 | (4) | 7-5-12[1] | |
| | 5-amino-2-thiophenecarboxylic acid | | HS-pyrrolidine-N(alloc)-C(O)NH-thiophene-CO₂H |
| 1-1 | (3) | 7-5-13[1] | |
| | 3-aminobenzoic acid | | HS-pyrrolidine-N(P(O)(OiPr)₂)-C(O)NH-3-carboxyphenyl |

1: Tri-n-butylphosphine may be added.

While certain preferred embodiments have been described herein in detail, numerous alternative embodiments are contemplated as falling within the scope of the invention.

What is claimed is:

1. A process of producing a compound of the formula 5:

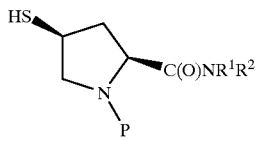

wherein P is diisopropylphosphoryl;

R¹ and R² are independently selected from hydrogen, aryl and heteroaryl, said aryl and heteroaryl groups being unsubstituted or substituted with from 1–3 groups selected from the group consisting of: $C_{1-4}$ alkyl, $C_{1-4}$ alkoxy, $C_{1-4}$ alkylthio, halo, hydroxy, $CO_2H$, $CO_2C_{1-4}$ alkyl, $NH_2$, $NHC_{1-4}$ alkyl, $N(C_{1-4}$ alkyl$)_2$, $SO_3H$, CN, $NHC(O)C_{1-4}$ alkyl, $SO_2NH_2$, $SO_2C_{1-4}$ alkyl, aryl and heteroaryl;

comprising: (a) reacting a compound of the formula 2:

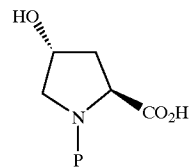

wherein P is as previously defined with diphenylphosphinic chloride to produce a compound of the formula 3:

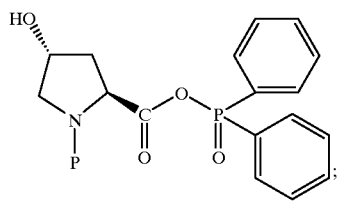

(b) reacting compound 3 with methanesulfonyl chloride to produce a compound of formula 4:

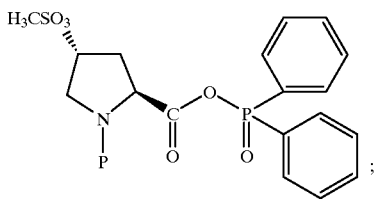

(c) combining compound 4 with an alkali metal sulfide or non-alkali metal sulfide in water to produce a compound of formula 1:

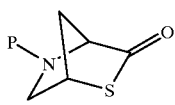

and (d) reacting compound 1 with $NHR^1R^2$ in the presence of an organic acid wherein $R^1$ and $R^2$ are as previously defined to produce a compound of formula 5.

2. A process in accordance with claim 1 wherein the organic acid is selected from formic acid, acetic acid and propionic acid.

3. A process in accordance with claim 1 wherein compound 2 is reacted with diphenylphosphinic chloride in the presence of a base.

4. A process in accordance with claim 3 wherein the base is a trialkylamine.

5. A process in accordance with claim 4 wherein the trialkylamine is selected from the group consisting of diisopropylethylamine and triethylamine.

6. A process in accordance with claim 1 wherein compound 3 is reacted with methanesulfonyl chloride to produce a compound of formula 4 in the presence of a base.

7. A process in accordance with claim 6 wherein the base is selected from the group consisting of pyridine, collidine and lutidine.

8. A process in accordance with claim 1 wherein $NHR^1R^2$ is selected from the group consisting of:

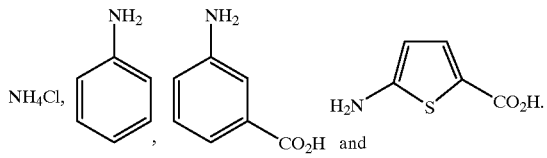

9. A process in accordance with claim 1 wherein the amine $HNR^1R^2$ is m-aminobenzoic acid.

10. A process in accordance with claim 1 further comprising reacting a compound of formula 5 with an acid to produce a compound of formula 6 or a salt or solvate thereof:

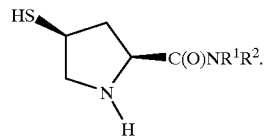

11. A process in accordance with claim 10 in which a trialkyl or triarylphosphine is optionally added.

12. A process in accordance with claim 11 in which the trialkylphosphine is tri-n-butylphosphine.

13. A process in accordance with claim 10 in which a solvent selected from the group consisting of $C_{1-5}$ alcohols, $C_{1-3}$ alkanoic acids, toluene, acetonitrile, ethyl acetate and others is optionally added.

14. A process in accordance with claim 10 in which the acid is hydrochloric acid.

15. A process in accordance with claim 1 wherein a compound of formula 2':

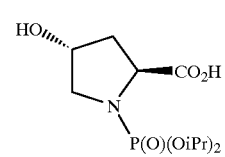

is reacted with diphenylphosphinic chloride to produce a compound of formula 3':

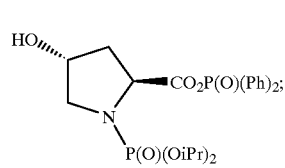

compound 3' is reacted with mesyl chloride to produce a compound of formula 4':

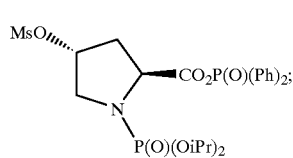

compound 4' is reacted with a member selected from the group consisting of: $Na_2S$, $K_2S$, CaS and BaS to produce a compound of formula 1':

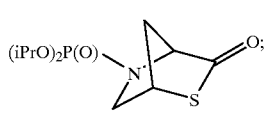

compound 1' is reacted with m-aminobenzoic acid to produce 5':

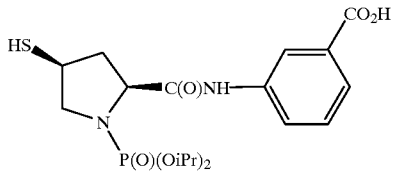

and compound 5' is reacted with acid to produce a compound of formula 6':

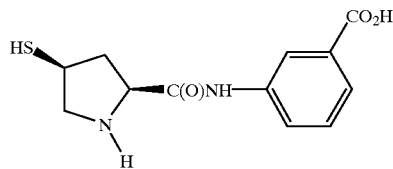

or a salt or solvate thereof.

16. A process in accordance with claim 15 in which a trialkyl or triarylphosphine is optionally added.

17. A process in accordance with claim 16 in which the trialkylphosphine is tri-n-butylphosphine.

18. A process in accordance with claim 15 in which 6' is crystallized from the group of solvents selected from $C_{1-5}$ alcohols, $C_{1-3}$ alkanoic acids, toluene, acetonitrile, ethyl acetate and others.

* * * * *